(12) United States Patent
Kamentsky (10) Patent No.: US 7,424,371 B2
(45) Date of Patent: Sep. 9, 2008

(54) NUCLEIC ACID ANALYSIS

(75) Inventor: Lee D. Kamentsky, Arlington, MA (US)

(73) Assignee: Helicos Biosciences Corporation, Cambridge, MA (US)

( * ) Notice: Subject to any disclaimer, the term of this patent is extended or adjusted under 35 U.S.C. 154(b) by 426 days.

(21) Appl. No.: 11/018,515

(22) Filed: Dec. 21, 2004

(65) Prior Publication Data

US 2006/0136144 A1    Jun. 22, 2006

(51) Int. Cl.
*G06F 19/00* (2006.01)
*G06F 7/60* (2006.01)
*G01N 33/48* (2006.01)

(52) U.S. Cl. .............................. 702/20; 702/19; 703/2

(58) Field of Classification Search ....................... None
See application file for complete search history.

(56) References Cited

OTHER PUBLICATIONS

Metzker, Michael, Emerging technologies in DNA sequencing, Genome Research, vol. 15, No. 12, Dec. 2005, pp. 1767-1776.

Sanger, F. et al., DNA sequencing with chain-terminating inhibitors, Proceedings of the National Academy of Sciences, USA, vol. 74, No. 12, Dec. 1977, pp. 5463-5467).

Maxam, A. et al., A new method for sequencing DNA, Proceedings of the National Academy of Sciences, USA, vol. 74, No. 2, Feb. 1977, pp. 560-564).

International Search Report and Written Opinion of the International Searching Authority for International Application No. PCT/US2005/045920, dated Jun. 1, 2006.

Braslavsky et al., "Sequence Information Can be Obtained from Single DNA Molecules," *PNAS*, 100(7):3960-3964 (2003).

*Numerical Recipes In C: The Art of Scientific Computing*, 332-336, 338-341 (ISBN 0-521-43108-5 Cambridge Univ. Press 1988).

*Primary Examiner*—Jason M Sims
(74) *Attorney, Agent, or Firm*—Cooley Godward Kronish LLP; Thomas C. Meyers; Konstanin M. Linnik (57) ABSTRACT

A sample nucleic acid sequence is compared against a database to find a matching sequence. In one embodiment, this comparison is accomplished with a table look-up approach that involves using sequences with collapsed homopolymer regions.

5 Claims, 6 Drawing Sheets

NUCLEIC ACID ANALYSIS

TECHNICAL FIELD

The invention relates to analyzing nucleic acid sequence data.

BACKGROUND

Completion of the human genome has paved the way for important insights into biologic structure and function. Knowledge of the human genome has given rise to inquiry into individual differences, as well as differences within an individual, as the basis for differences in biological function and dysfunction. For example, single nucleotide differences between individuals, called single nucleotide polymorphisms (SNPs), are responsible for dramatic phenotypic differences. Those differences can be outward expressions of phenotype or can involve the likelihood that an individual will get a specific disease or how that individual will respond to treatment. Moreover, subtle genomic changes have been shown to be responsible for the manifestation of genetic diseases, such as cancer. A true understanding of the complexities in either normal or abnormal function will require large amounts of specific sequence information.

An understanding of cancer also requires an understanding of genomic sequence complexity. Cancer is a disease that is rooted in heterogeneous genomic instability. Most cancers develop from a series of genomic changes, some subtle and some significant, that occur in a small subpopulation of cells. Knowledge of the sequence variations that lead to cancer will lead to an understanding of the etiology of the disease, as well as ways to treat and prevent it. An essential first step in understanding genomic complexity is the ability to perform high-resolution sequencing.

Various approaches to nucleic acid sequencing exist. One conventional way to do bulk sequencing is by chain termination and gel separation, essentially as described by Sanger et al., Proc. Natl. Acad. Sci., 74(12): 5463-67 (1977). That method relies on the generation of a mixed population of nucleic acid fragments representing terminations at each base in a sequence. The fragments are then run on an electrophoretic gel and the sequence is revealed by the order of fragments in the gel. Another conventional bulk sequencing method relies on chemical degradation of nucleic acid fragments. See, Maxam et al., Proc. Natl. Acad. Sci., 74: 560-564 (1977). Finally, methods have been developed based upon sequencing by hybridization. See, e.g., Drmanac, et al., Nature Biotech., 16: 54-58 (1998).

Bulk sequencing techniques are not useful for the identification of subtle or rare nucleotide changes due to the many cloning, amplification, and electrophoresis steps that complicate the process of gaining useful information regarding individual nucleotides. The ability to sequence and gain information from single molecules obtained from an individual patient is the next milestone for genomic sequencing. As such, research has evolved toward methods for rapid sequencing, such as single molecule sequencing technologies.

There have been many proposals to develop new sequencing technologies based on single-molecule measurements, generally either by observing the interaction of particular proteins with DNA or by using ultra high resolution scanned probe microscopy. See, e.g., Rigler, et al., *DNA-Sequencing at the Single Molecule Level*, Journal of Biotechnology, 86(3): 161 (2001); Goodwin, P. M., et al., *Application of Single Molecule Detection to DNA Sequencing*. Nucleosides & Nucleotides, 16(5-6): 543-550 (1997); Howorka, S., et al., *Sequence-Specific Detection of Individual DNA Strands using Engineered Nanopores*, Nature Biotechnology, 19(7): 636-639 (2001); Meller, A., et al., *Rapid Nanopore Discrimination Between Single Polynucleotide Molecules*, Proceedings of the National Academy of Sciences of the United States of America, 97(3): 1079-1084 (2000); Driscoll, R. J., et al., *Atomic-Scale Imaging of DNA Using Scanning Tunneling Microscopy*. Nature, 346(6281): 294-296 (1990). Unlike conventional sequencing technologies, their speed and read-length would not be inherently limited by the resolving power of electrophoretic separation. Other methods proposed for single molecule sequencing include detecting individual nucleotides as they are incorporated into a primed template, i.e., sequencing by synthesis.

A significant issue in single molecule sequencing techniques is the presence of homopolymeric regions in sample nucleic acids. Homopolymers are stretches of an identical base that are found throughout the genomes of most organisms. In single molecule experiments, one or more nucleotides are introduced to a template primer complex in the presence of polymerase. Template-dependent nucleotide incorporation takes place as the primer is elongated. However, when the template contains a homopolymer, it is often difficult to determine whether a signal indicating nucleotide incorporation is due to the incorporation of a single nucleotide or to multiple members of the same nucleotide species (e.g., adenine, guanine, thymine, cytosine, uracil, or their analogs) in a homopolymeric stretch on the template. The inability to resolve homopolymers can lead to problems in correctly analyzing and positioning sequence fragments in the genome. The invention addresses this and other problems associated with nucleic acid sequence information processing.

SUMMARY OF THE INVENTION

The invention relates to analyzing nucleic acid sequence data. According to one aspect of the invention, sequences obtained from a sample are collapsed into a format that is easily compared against sequence entries in a look-up table, while preserving the informational content of the sequences. In particular, this aspect of the invention comprises collapsing homopolymer regions in sample sequences such that homopolymers are represented by a single nucleotide.

A database of reference genomic sequences in which homopolymer regions are represented by a single nucleotide base (e.g., "AAAAAA" is reduced to "A") can be utilized as a look-up table for comparison to sequence data obtained from a biological sample. Sample-derived sequences in which homopolymers are also reduced to a single representative nucleotide are compared to the database in order to determine if they match a database sequence. A match can be an exact match or a best fit such as a closest non-exact match. Matching sequences are identified as being present in the genomic sample from which the reference population was obtained. The matched sequences can also be expanded back to their unreduced form (i.e., including homopolymer regions) for further mapping and/or analysis.

In some aspects of the invention, indexes and comparison functions can be used to match sequences, in some instances without the need explicitly to create reduced or collapsed sequence strings.

Another way of matching sequences can involve creating a table of fixed-length reduced sequence strings that are ordered lexically, where each string has an associated list of sites in a main database at which the string appears. Still another way is to create a table of fixed-length unreduced strings and to use the indexes and comparison functions that are referred to above and that are described in greater detail below in the description section.

The invention also provides for the use of a database with entries that contain known or suspected sequence errors. It is often desirable to determine whether a sample sequence contains base additions, deletions, substitutions, transpositions, translocations, or other changes from what one would expect in a wild-type sequence. Thus, a database can be constructed to include members with known or unknown sequence changes with respect to the wild-type sequence. In one embodiment, a database contains all possible unique sequences of a predetermined length (e.g., all 25-mers). In another embodiment, a database contains all unique sequences known or suspected to be involved in a particular pathology, such as cancer. Other databases contain one or more types of sequence "errors", including deletions, additions (either of which might result in a shift or offset of the database sequence with respect to the wildtype), translocations, inversions, and others.

In one aspect of the invention, a sequence identified from a patient sample is compared to a database of reference nucleic acid sequences to determine a match. The match may be an exact match or an approximate match within a predetermined limit. The reference sequences may represent, for example, nucleic acid sequences from a virus, bacterium, or other foreign organism; human nucleic acid sequences indicative of the presence of a medical condition such as cancer, or of a likelihood of developing the condition, or of a preferred course of treatment; or a set of nucleic acids from one or more healthy reference subjects, such as the set of RNA transcripts expressed in a particular tissue or a normal complement of human genomic DNA. By collapsing homopolymer regions in the entries in the reference sequence database, the amount of data in the database and the size of the database is reduced, thereby reducing memory and/or storage requirements as well as processing capacity requirements for a computer or computer network that is storing and allowing access to the reduced database. Particularly where very large numbers of measured sequences are generated, as in single molecule sequencing, the timesavings associated with conducting millions of sequence comparisons against a database of reduced size is substantial.

The invention relates to storing and allowing access to entries or members of a database or table where the entries or members are unique nucleic acid sequences without homopolymer regions. A computer-readable medium in which the data are stored may contain, for example, thousands, millions, or billions of these reference sequences. Generally, the reference sequences included in the database or table are sequences representative of genomic DNA, cDNA, or RNA (e.g., messenger RNA, ribosomal RNA, siRNA) or other nucleic acid sequences of interest. The unique nucleic acid sequences preferably fall within a particular size range, such as between about 15 to about 100 nucleotides in length. The sequence representations can be of uniform or variable length. For example, if all sequence representations are derived from nucleic acid sequences of a fixed length prior to the collapse of homopolymer regions, each of the resulting collapsed nucleic acid sequences would then have a variable length depending on the length and number of associated homopolymer regions that exist prior to the collapse. Alternatively, sequence representations may exhibit uniform lengths in embodiments in which homopolymer regions are first collapsed to single nucleotides and then sequences of a desired length are formed.

The invention permits comparison of a collapsed representation of a nucleic acid sequence from a sample to a database of reference nucleic acids without homopolymer regions. In many instances, this provides sufficient information to identify the nucleic acid sequence from the sample as being of interest (e.g., identifying the nucleic acid as corresponding to a particular mRNA, or to a particular pathogen, or to a particular disease-linked mutation). If, however, the length of a homopolymer region is also relevant, the invention permits such a comparison. Initially, a collapsed representation of a sample nucleic acid sequence is compared to a database of reference nucleic acid sequences without homopolymer regions (i.e., sequences in which any homopolymer regions have been collapsed to a single nucleotide). In addition to the collapsed versions of the reference sequences, the database itself, or in conjunction with other databases, can also store and allow access to information related to and indicative of the original, non-collapsed sequences that include the homopolymer regions. For example, collapsed and non-collapsed sequences may be stored within a common database, collapsed sequences may be stored in separate databases relative to non-collapsed sequences with pointers and/or other types of links or indicia enabling traversal therebetween, and/or collapsed sequences may be stored along with indicia (e.g., pointers, position offsets, etc.) that enables the non-collapsed sequences associated therewith to be dynamically formed or determined therefrom. Further, several original (i.e., non-collapsed) sequences may correspond to a single reference nucleic acid sequence in the database if, after collapse of homopolymer regions, the resulting sequences are the same. In such instances, indicia can be stored within the database that identifies the genomic location of the identical sequences, while avoiding the duplication of entries of the sequences themselves in the database. Accordingly, the number of entries in the database can be further reduced, thereby further reducing computer and/or network resource requirements and accelerating access to and/or searches of the database entries.

Further features, aspects, and advantages of the invention are described and illustrated in the following description and drawings.

BRIEF DESCRIPTION OF THE DRAWINGS

The drawings are not necessarily to scale, emphasis instead generally being placed upon illustrating the principles of the invention.

DESCRIPTION

Unless otherwise specified, the illustrated embodiments can be understood as providing exemplary features of varying detail of certain embodiments, and therefore, unless otherwise specified, features, components, modules, elements, and/or aspects of the illustrations can be otherwise combined, interconnected, sequenced, separated, interchanged, positioned, and/or rearranged without materially departing from the disclosed systems or methods. Additionally, the shapes and sizes of components/elements are also exemplary and unless otherwise specified, can be altered without materially affecting or limiting the disclosed technology.

One or more digital data processing devices can be used in connection with various embodiments of the invention. Such a device generally can be a personal computer, computer workstation (e.g., Sun, HP), laptop computer, server computer, mainframe computer, handheld device (e.g., personal digital assistant, Pocket PC, cellular telephone, etc.), information appliance, or any other type of generic or special-purpose, processor-controlled device capable of receiving, processing, displaying, and/or transmitting digital data. A processor generally is logic circuitry that responds to and processes instructions that drive a digital data processing device and can include, without limitation, a central processing unit, an arithmetic logic unit, an application specific integrated circuit, a task engine, and/or any combinations, arrangements, or multiples thereof. Software or code generally refers to computer instructions which, when executed on one or more digital data processing devices, cause interactions with operating parameters, sequence data/parameters, database entries, network connection parameters/data, variables, constants, software libraries, and/or any other elements needed for the proper execution of the instructions, within an execution environment in memory of the digital data processing device(s). Those of ordinary skill will recognize that the software and various processes discussed herein are merely exemplary of the functionality performed by the disclosed technology and thus such processes and/or their equivalents may be implemented in commercial embodiments in various combinations and quantities without materially affecting the operation of the disclosed technology.

As is known to those of ordinary skill, a network can be a series of network nodes (each node being a digital data processing device, for example) that can be interconnected by network devices and communication lines (e.g., public carrier lines, private lines, satellite lines, etc.) that enable the network nodes to communicate. The transfer of data (e.g., messages) between network nodes can be facilitated by network devices such as routers, switches, multiplexers, bridges, gateways, etc. that can manipulate and/or route data from an originating node to a destination node regardless of any dissimilarities in the network topology (e.g., bus, star, token ring, etc.), spatial distance (local, metropolitan, wide area network, etc.), transmission technology (e.g., TCP/IP, Systems Network Architecture, etc.), data type (e.g., data, voice, video, multimedia, etc.), nature of connection (e.g., switched, non-switched, dial-up, dedicated, virtual, etc.), and/or physical link (e.g., optical fiber, coaxial cable, twisted pair, wireless, etc.) between the originating and destination network nodes.

In brief overview, the disclosed technology relates to comparing nucleic acid sequence information obtained from a biological sample against a collection of reference nucleic acid sequences. Different collections of reference sequences can be created and used depending on what one is trying to determine about the sample sequence. For example, reference sequences associated with a particular disease may be stored in one or more databases, tables, and/or types of data repositories and may be subsequently compared with one or more sample sequences to determine whether a patient from which the sample sequences were obtained/determined has that disease. The disclosed technology can facilitate the formation and/or population of such data repositories, as well as facilitate comparisons involving data stored therein.

In one illustrative embodiment, the disclosed technology is used to develop systems and perform methods in which homopolymer regions in one or more nucleic acid sequences are collapsed into single nucleotides, thereby creating reduced-size sequence representations that require less memory, processing, and/or network resources and that expedite desired nucleic acid processing and analysis activities. In some illustrative embodiments, the database is represented in such a way, through the use of indexes (and perhaps without explicitly creating collapsed sequence strings), to also result in reduced computational requirements.

In accordance with one aspect of the invention, a database contains entries that do not have any homopolymer regions and such entries may represent any desired population of nucleic acids against which one wishes to compare a sequence obtained from a sample. For example, a database may comprise all possible 25-mers lacking a homopolymer region. Alternatively, a database may contain all sequences of a given length in a particular species' genome (e.g., all 25-mers present in the human genome). The database may contain a subset of genomic DNA or RNA. For example, the database may contain all oncogene sequences of a predetermined length or all messenger RNA sequences of a predetermined length. The length of the sequences may be determined by the complexity of the database and/or the resolution desired in matching a sample sequence against the database. For example, the longer the individual sequences in the database, the fewer matches, on average, are expected between a reference sequence in the database and a sequence derived from a sample.

Figure 1:
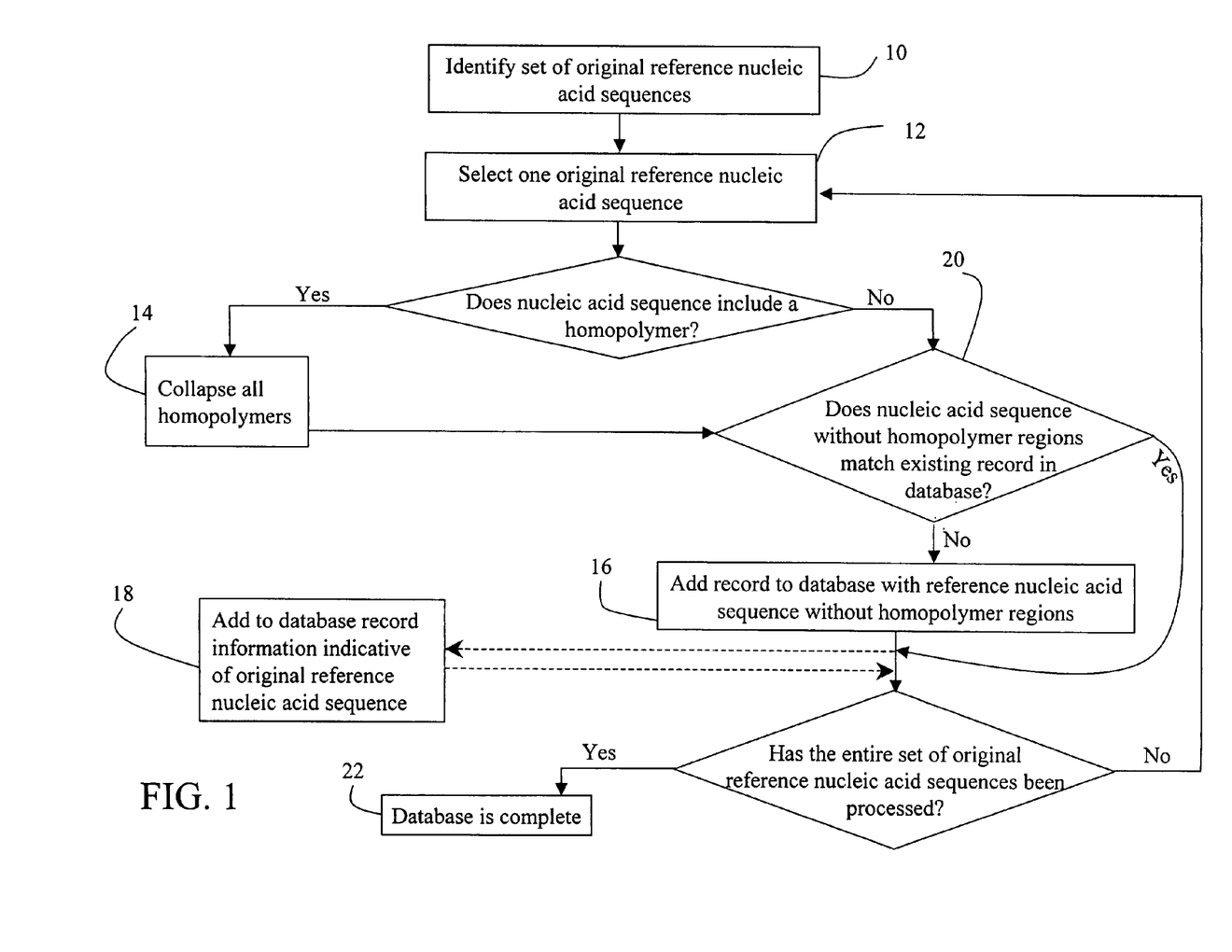
FIG. 1 is a flowchart representation of one exemplary way of generating a database of reference nucleic acid sequences without homopolymer regions.

In one illustrative operation and with reference to FIG. 1, the disclosed technology is used to identify one or more sets of original (i.e., non-collapsed) reference nucleic acid sequences of interest (10) and to select one or more particular reference nucleic acid sequences in the sets for further processing (12). If the selected reference nucleic acid sequence contains at least one homopolymer region, all homopolymer regions in the selected sequence are collapsed to a single nucleotide to form a reference nucleic acid sequence without homopolymer regions (14). A database record incorporating this collapsed reference nucleic acid sequence, or incorporating the original reference nucleic acid sequence if it originally contained no homopolymer regions, can be added to a new database of reference nucleic acids without homopolymer regions. The added database record and/or other related database records may optionally store information that facilitates subsequent expansion of the collapsed reference nucleic acid sequence into its original non-collapsed form (18). For example, the database record can include a) genome location information that enables a particular collapsed sequence to be mapped to its non-collapsed counterpart in a genome of interest, b) pointers and/or other types of links or indicia that uniquely identify locations and/or database records within one or more databases (may be the same or a different database) that store corresponding non-collapsed reference nucleic acid sequences, c) position offset and/or pointer information indicative of how/where particular nucleotides repeat in a non-collapsed sequence that enables the dynamic regeneration of the non-collapsed sequence from the corresponding collapsed sequence, and/or any other information that facilitates identification and/or formation of a non-collapsed sequence of interest. This database record information can be maintained for reference nucleic acid sequences, as well as for nucleic acid sequences associated with a biological sample.

An additional original reference nucleic acid sequence can then be selected from the initial set and the process is repeated until the entire set of original reference nucleic acid sequences has been processed. When an additional original reference nucleic acid is processed, a new database record incorporating the reference nucleic acid without homopolymer regions is added only if the reference nucleic acid without homopolymer regions is new, i.e., is not already present in the new database (16). Alternatively, a second record is added to the database incorporating the identical reference sequence, but having other attributes (such as a reference to a record containing the associated non-collapsed sequence) that distinguish it from the first sequence. Accordingly, each of the selected reference nucleic acid sequences without homopolymer regions is compared to existing reference nucleic acids in the database to ascertain whether it has been previously encountered (20). In the event of a match, information regarding the original reference nucleic acid with any homopolymer regions is optionally added to the matched database record (18) and a new original reference nucleic acid sequence is selected to continue the process of building the database (12). On the other hand, if there is no match, a new record incorporating the reference nucleic acid sequence without homopolymer regions is added to the database of reference nucleic acids without homopolymer regions (16) and information regarding the original reference nucleic acid with any homopolymer regions is optionally added (18). Once all original reference nucleic acid sequences from the set have been selected and processed, the database is complete (22). An illustrative database of mRNA sequences without homopolymer regions that may be formed in accordance with the exemplary methodology of FIG. 1 is described below in connection with Example 1.

Once the database is complete, it includes records incorporating each reference nucleic acid sequence without homopolymer regions. As previously discussed, the database can also optionally incorporate information regarding the original reference nucleic acid sequences, which may contain one or more homopolymer regions. This information can be used to re-expand the collapsed sequences (i.e., reference nucleic acid sequences without homopolymer regions) stored in the database into their original, non-collapsed form. Each record in the database is preferably unique, i.e., each reference nucleic acid sequence without homopolymer regions is preferably present in only one record in the database. Accordingly, a single representative entry within the database may be made for duplicative collapsed sequences and information (e.g., genomic location information) indicative of the multiple occurrences of any such duplications can also be stored within the corresponding database record for subsequent retrieval and analysis.

A database of reference nucleic acid sequences can be used as a look-up table. Comparing a nucleic acid sequence of a sample to the reference nucleic acid sequences in a look-up table can provide identification and/or other types of information that can be used to catalogue or otherwise describe/define the nucleic acid sequence of the sample. In some instances, the mere presence of a match to the look-up table may be informative, such as that described below in connection with Example 2 in which sequenced cDNA molecules are matched to mRNA transcripts. A look-up table can also be used to index a database of non-collapsed nucleic acid sequences and optionally contains additional information regarding, for example, location of a sequence within a transcript or within a genome.

In general, there are various techniques that can be used to find a match among members of a sequence database. One matching scheme involves, as previously mentioned, creating a new reference database in which homopolymer regions are reduced to a single base, optionally linking each position in the new database with its position in the old or original database using an index or pointer. The sample sequence string is then likewise reduced and compared against the reference sequence up to the end of the length of the sample sequence (which in general can be of any length). In this approach, the comparison generally is done with an index that is built on the reference data set.

Another matching scheme uses an index into the original database of non-collapsed reference sequences. That scheme uses an index array that is a vector of pointers into the database, and the pointers are ordered in increasing value of the elements to which they point. The indexes require a matching algorithm to provide the ordering of elements. In one embodiment, the elements consist of the sequence strings, and in each string there are the symbols A, C, G, and T, as well as and end-of-string symbol such as "0". The matching algorithm between two pointers is, in the C programming language:

```
boolean less(char *ptr1, char *ptr2)    /* returns true if ptr1 is less than
                                            ptr2 */
{
    while(true) {
        if (*ptr2=='0') return false;
        if (*ptr1=='0') return true;
        if (*ptr1!=*ptr2) return *ptr1<*ptr2;
        do ptr1++; while ptr1[0] == ptr1[-1];
        do ptr2++; while ptr2[0]==ptr2[-1];
    }
}
```

In this matching scheme, the sample sequence can be of any length, and the reference database does not need to contain reference sequences of a given length. Both this matching scheme and the prior one can produce the same index table.

In accordance with the matching scheme described in the preceding paragraph, one way of handling a database of reference nucleic acid sequences (different from the exemplary way shown in and described with respect to FIG. 1) can involve the following steps. First, append the symbol "0" to the end of each sequence, such that, for example, "AGCT" becomes "AGCT0". Second, create an empty vector "V1" that will hold the concatenation of all sequences. Third, create an empty vector "V2" of records where each record holds the offset of the start of each sequence in V1 and a pointer to the annotation data for that sequence (such as its name or significance). Fourth, create an empty vector "V3" that will hold one offset into V1 for each base that is different from the previous base. Fifth, add the next sequence to V1 (e.g. "AGCT0"+ "GCGC0" becomes "AGCT0GCGC0", and add a record to V2 containing the offset in V1 of the start of the sequence. Sixth, for each base in the sequence that is different from the previous base, append a record containing the offset to that base to V3. This makes V3 a vector of offsets to the first base of any homopolymer or single base not followed by a repeat. If there are more reference sequences to handle, go to the fifth step. If not, go to the eighth step which is to sort V3. The quicksort algorithm can be used for this, except that the algorithm in the preceding paragraph is used as the sort criterion. The quicksort algorithm is a known fast sorting algorithm.

See, for example, chapter 8.2 entitled "Quicksort" of the book "Numerical Recipes in C: The Art of Scientific Computing" (ISBN 0-521-43108-5, copyright 1988-1992 by Cambridge University Press, pp. 332-336). The result of these steps is (1) a vector of offsets to positions in the concatenated sequence string, sorted by ascending order in the sort criterion, and (2) a vector of offsets to starts of sequences and pointers to the sequence annotations, sorted by ascending offset into the concatenated sequence string. Both of these vectors can be stored (e.g., on or in a computer-readable medium 142) and searched efficiently using a binary search, such as the binary search described in chapters 8.4 and 8.5 entitled "Indexing and Ranking" and "Selecting the Mth Largest", respectively, of the book "Numerical Recipes in C: The Art of Scientific Computing" (ISBN 0-521-43108-5, copyright 1988-1992 by Cambridge University Press, pp. 338-341).

Carrying on from the preceding paragraph, the binary search involves picking a middle reference sequence of the sorted array and determining if the sample sequence being compared is greater or less than this picked reference sequence according to the sort criterion. If it is greater, then repeat with the upper half of the sorted array. If it is less, then repeat with the lower half of the sorted array until a single element is identified. This matching scheme thus requires a maximum number of comparisons that is equal to the number of binary digits in the index of the last element in the array. For example, if there are 4096 elements in the array, that corresponds to 12 binary digits (because 2 to the $12^{th}$ power equals 4096), and thus with such an array the number of comparisons would be at most 12 as opposed to the maximum of 4096. The comparison method shown in and described with respect to FIG. 4 could involve (worst case) comparing the sample sequence against every entry in the reference database to find a match or best fit, whereas the binary search here described typically will involve far fewer comparisons to find a match or best fit and thus is generally much more efficient.

Yet another matching scheme involves creating a table of fixed-length reduced sequence strings, and ordering them lexically. Each string has an associated list of sites in the original database at which the string appears. Still another matching scheme involves creating a table of fixed-length, non-collapsed sequence strings and then using the matching algorithm described above.

Figure 2:
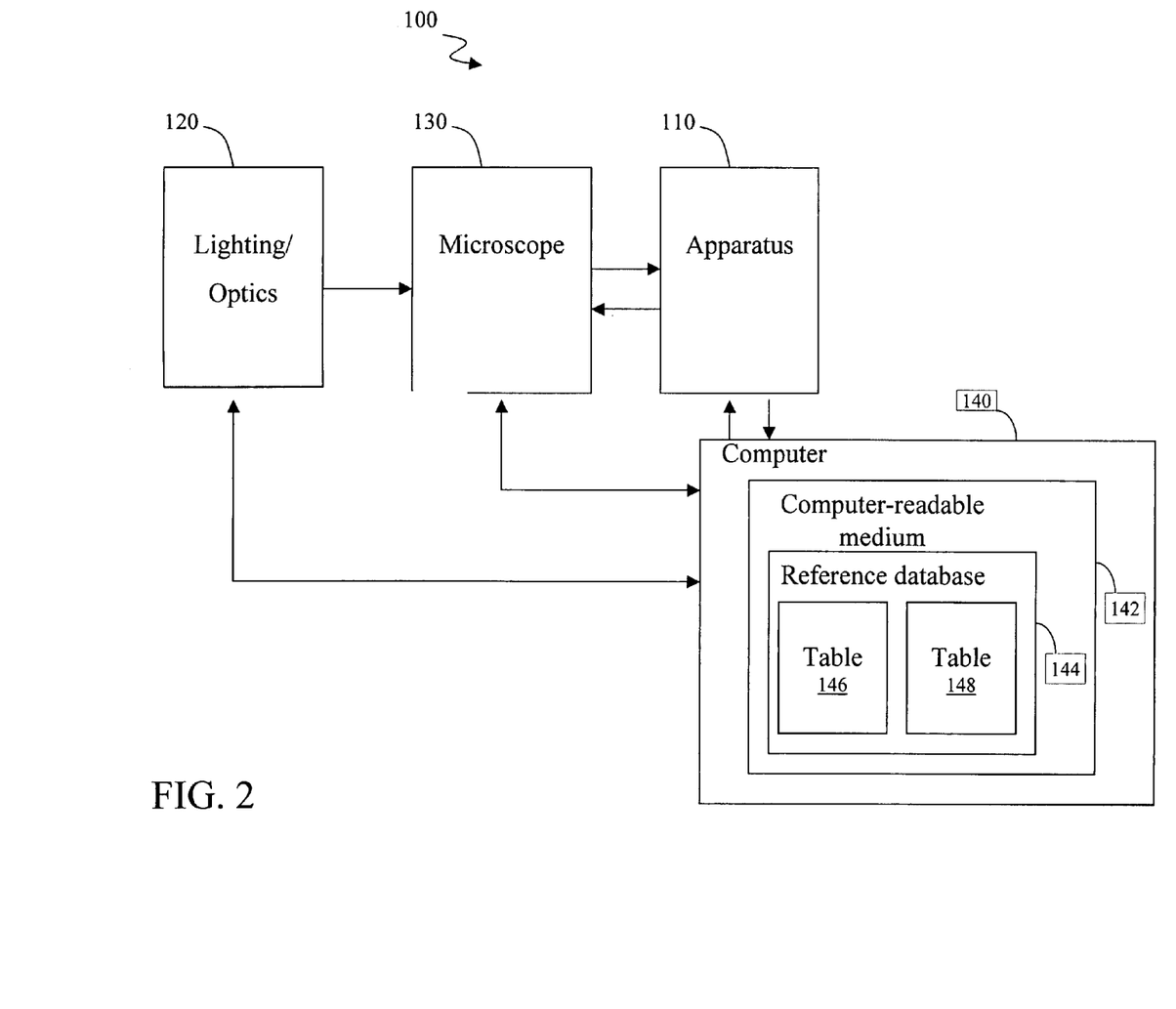
FIG. 2 schematically illustrates one exemplary system for collecting and comparing sequence data.

In some embodiments, one or more look-up tables can be used to analyze the results of DNA sequencing methods, particularly for high-throughput sequencing methods. An exemplary system that may be used to perform single-molecule sequencing is shown in FIG. 2. System 100 permits sequencing by synthesis of a nucleic acid from a sample. System 100 includes an apparatus 110 for handling microfluidic volumes and also includes other components including a lighting/optics module 120, a microscope module 130, and a digital data processing device 140. These elements communicate with and/or interrelate to one another generally as shown by the arrows in FIG. 2.

The lighting/optics module 120 can include multiple light sources and filters to provide light to a microscope of the microscope module 130 for viewing and analysis. The light is reflected onto a flow cell that has the sample therein or thereon and that is seated near (e.g., above or below) the microscope. The microscope module 130 includes hardware for holding the flow cell and moving a microscope stage and an imaging device. The digital data processing device 140 includes and/or is communicatively coupled to at least one computer-readable medium 142 containing a reference sequence database 144. By way of non-limiting example, a computer-readable medium 142 can include a variety of memory types and memory storage devices, such as, for example, one or more volatile memory elements (e.g., random access memory), nonvolatile memory elements (e.g., read only memory, EEPROM, etc.), hard drives, floppy drives, floptical drives, CD-ROMs, DVDs, USB memory sticks, and/or any other type of memory or device, separately or in any combination or multitude, that may be used to store and/or access computer-executable instructions and/or digital data (e.g., database records, nucleic acid sequences, etc.) necessary for the proper operation of the disclosed technology. As is known to those skilled in the art, a digital data processing device 140 can include, without limitation, one or more computer-readable media, processor(s), devices, controllers, user interfaces, software programs, and/or any other computer components necessary for operating the system 100 in accordance with the disclosed technology for storing, accessing, and/or analyzing nucleic acid sequence information.

In one illustrative operation, a nucleic acid from a sample is fragmented and immobilized in a flow cell. The nucleic acid in the flow cell includes a primer binding site to which a complementary primer nucleic acid has hybridized. The apparatus 110 injects into the flow cell a solution comprising a fluorescent nucleotide and a polymerase in a buffered solution under conditions permitting incorporation of the fluorescent nucleotide at the 3' end of the primer, if and only if the fluorescent nucleotide is complementary to the first position of the nucleic acid. Apparatus 110 then injects a wash solution to remove any unincorporated nucleotides and the lighting/optics module 120 then detects the presence or absence of fluorescence at the location of the nucleic acid, which is recorded by the digital data processing device 140. The fluorescent nucleotide can then be bleached or the fluorescent label is removed and the apparatus 110 injects a different nucleotide/polymerase/buffer solution. System 100 iterates the process until enough sequence information for a sample of interest has been recorded by the digital data processing device 140 to permit comparison of the recorded sample sequence to the entries in the reference sequence database 144 contained on or in the computer-readable medium 142.

Figure 3:
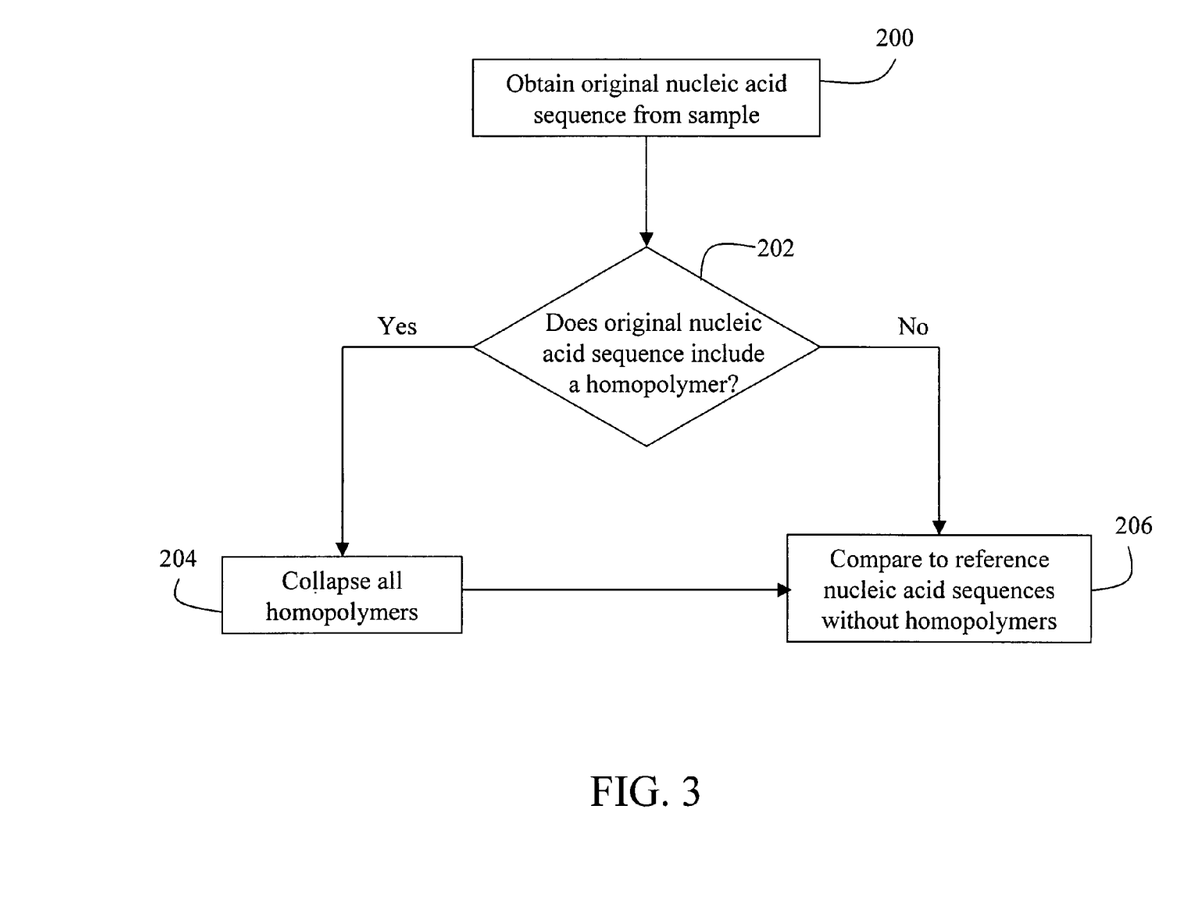
FIG. 3 is a flowchart representation of one exemplary way of comparing sequences.

In one illustrative embodiment and with reference to FIG. 3, an original (i.e., non-collapsed) nucleic acid sequence of a sample can be obtained from the system of FIG. 2 (200) and can be analyzed (by, for example, one or more software processes executing on the digital data processing device 140) to ascertain whether such sequence includes one or more homopolymer regions (202). If one or more homopolymer regions are encountered within the sample's nucleic acid sequence, these regions can be collapsed into a single base of the same type present in each homopolymer (e.g., "AAAAA" becomes "A") (204). The collapsed nucleic acid sequence of the sample (i.e., without any homopolymer regions) is then compared to a database of reference nucleic acid sequences that also do not include homopolymer regions (206).

An exemplary algorithm for collapsing homopolymer regions within the nucleic acid sequences of a sample of interest is described in the following example. A nucleic acid sequence "AAGGGCT" is detected by system 100 (see FIG. 2) at one position in the flow cell of apparatus 110 and the digital data processing device 140 records the nucleotide sequence as string "AAGGGCT." A software process executed by the digital data processing device 140 can read each symbol in the recorded string and append it to a second string only if the previous symbol is different. Exemplary actions that may be performed by a software process on a string is detailed in the following paragraph.

The software process reads the first nucleotide in the first string: "AAGGGCT." The program appends "A" to the second string; the sequence of the second string becomes "A." The software process reads the second nucleotide in the first string ("AAGGGCT"), and compares it to the last nucleotide of the second string ("A"). Because the two are the same, the software process makes no changes to the second string ("A") and proceeds to read the third nucleotide in the first string ("AAGGGCT"). Because the third nucleotide in the first string ("G") is different from the last nucleotide in the second string ("A"), the software process appends a "G" to the end of the second string, yielding a second string "AG." The software process reads the fourth nucleotide of the first string ("AAGGGCT") and compares it to the last nucleotide of the second string ("AG"). Because the two are the same, the software process makes no changes to the second string ("AG") and proceeds to read the fifth nucleotide of the first string ("AAGGGCT"). Because it is the same as the last nucleotide of the second string ("AG"), the software process makes no changes to the second string and proceeds to read the sixth nucleotide of the first string ("AAGGGCT"). Because the sixth nucleotide of the first string differs from the last nucleotide of the second string ("AG"), the software process appends a "C" to the end of the second string, yielding a second string "AGC." The process reads the last nucleotide in the first string ("AAGGGCT") and compares it to the last nucleotide in the second string ("AGC"). Because the two differ, the software process appends a "T" to the second string, yielding a final second string of "AGCT." In this manner, the homopolymer regions within the original nucleic acid sequence of a sample, "AAGGGCT," is collapsed into a nucleic acid sequence without homopolymer regions, "AGCT."

Figure 4:
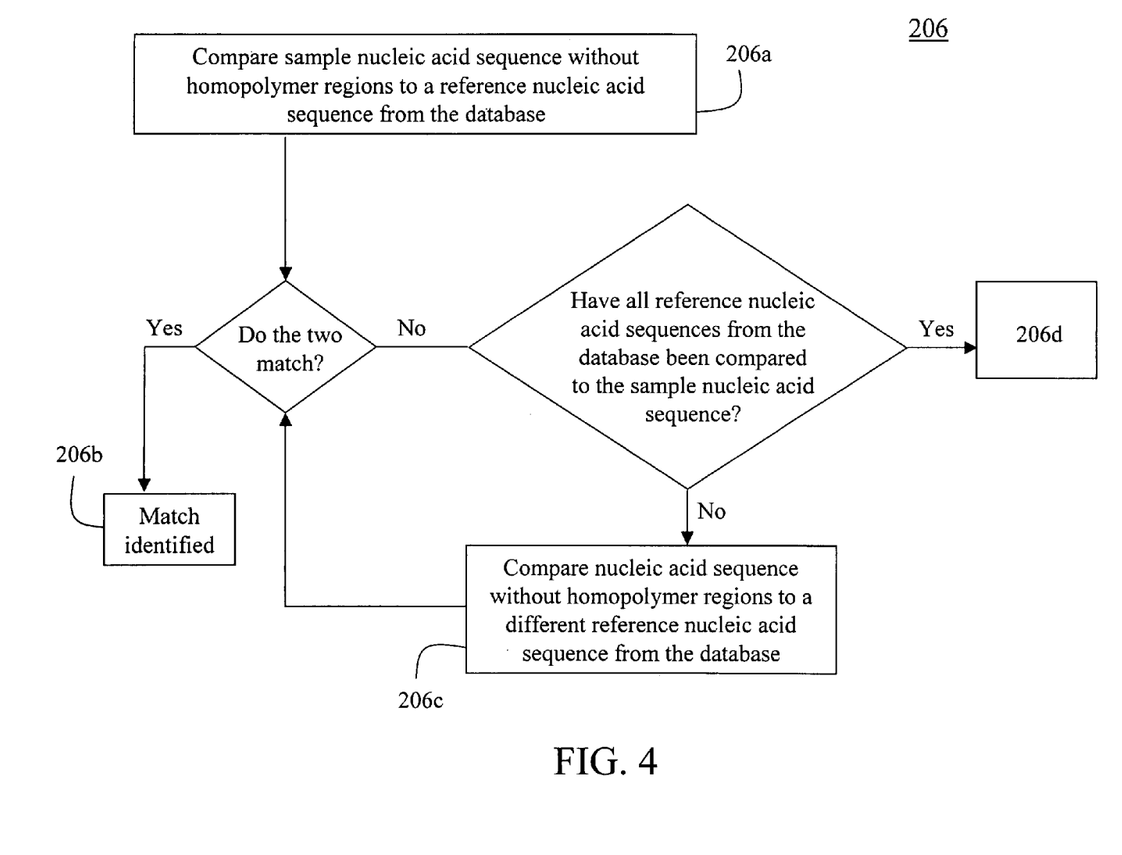
FIG. 4 is a flowchart detailing one exemplary way of comparing a sample nucleic acid sequence without homopolymer regions to a database of reference nucleic acid sequences without homopolymer regions.

With reference now also to FIG. 4, a comparison of collapsed nucleic acid sequences of a sample to collapsed reference nucleic acid sequences in a database may be performed iteratively. For example, with the same or a different software process executed by the digital data processing device 140, a first comparison can be made between a sample nucleic acid sequence without homopolymer regions and a reference nucleic acid sequence without homopolymer regions from the database (such as the first-listed reference sequence in table 146 of the reference database 144) (206a). If a match is identified (206b) by that first comparison, the software process executed by the digital data processing device 140 has completed the comparison of that sample sequence. Otherwise, if a match is not identified, the software process executed by the digital data processing device 140 makes a comparison between the sample sequence and another reference nucleic acid sequence from the database 144 (such as the second-listed reference sequence in table 146) (206c). The software process continues this table look-up process and approach until a match is identified (206b) or the entries in the table 146 are exhausted and no match is found (206d). The software program can operate in this iterative table look-up manner for any other collapsed sample nucleic acid sequences that are to be compared to entries in a table to find a match, and in this way a list of matching sequences can be generated by the software process and stored by the digital data processing device 140. Depending on the database or table used in the look-up process, the list of matching sequences may be, for example, a list of mutated sequences, a list of non-mutated sequences, or a list of sequences associated with a pathology.

In one comparison method, a binary search against an index is used to speed up searching and arrive sooner and faster at a match or best fit, as described previously.

In some embodiments, once matches to the database are identified, the process is complete. In other embodiments, it may also be useful to compare an original, non-collapsed sample nucleic acid sequence to one or more original, non-collapsed reference nucleic acid sequences. This additional comparison can be performed using optional information stored within one or more records of the database regarding the identity of the one or more original, non-collapsed reference/sample nucleic acid sequences which, when collapsed, correspond to the reference/sample nucleic acid sequences in the database.

For example, optional information may include genome location information for a collapsed reference nucleic acid sequence that can be used to query and/or index into an existing database of non-collapsed reference nucleic acid sequences to identify the particular non-collapsed reference nucleic acid sequence that corresponds to the collapsed reference nucleic acid sequence of interest. A similar approach can be performed for a collapsed sample nucleic acid sequence, if a non-collapsed set of sample nucleic acid sequences have been previously stored in a database. Alternatively or in combination, optional information can include pointers and/or other types of links or indicia that uniquely identify locations and/or database records within one or more databases (may be the same or a different database) that store corresponding non-collapsed reference/sample nucleic acid sequences, such that, for example, a database record associated with a collapsed reference/sample nucleic acid sequence may include a pointer to a database location storing the corresponding non-collapsed reference/sample nucleic acid sequence. In yet another example, optional information can include position offset and/or pointer information indicative of how/where particular nucleotides repeat in a non-collapsed reference/sample sequence that enables the dynamic regeneration of the non-collapsed sequence from the corresponding collapsed sequence.

Figure 5:
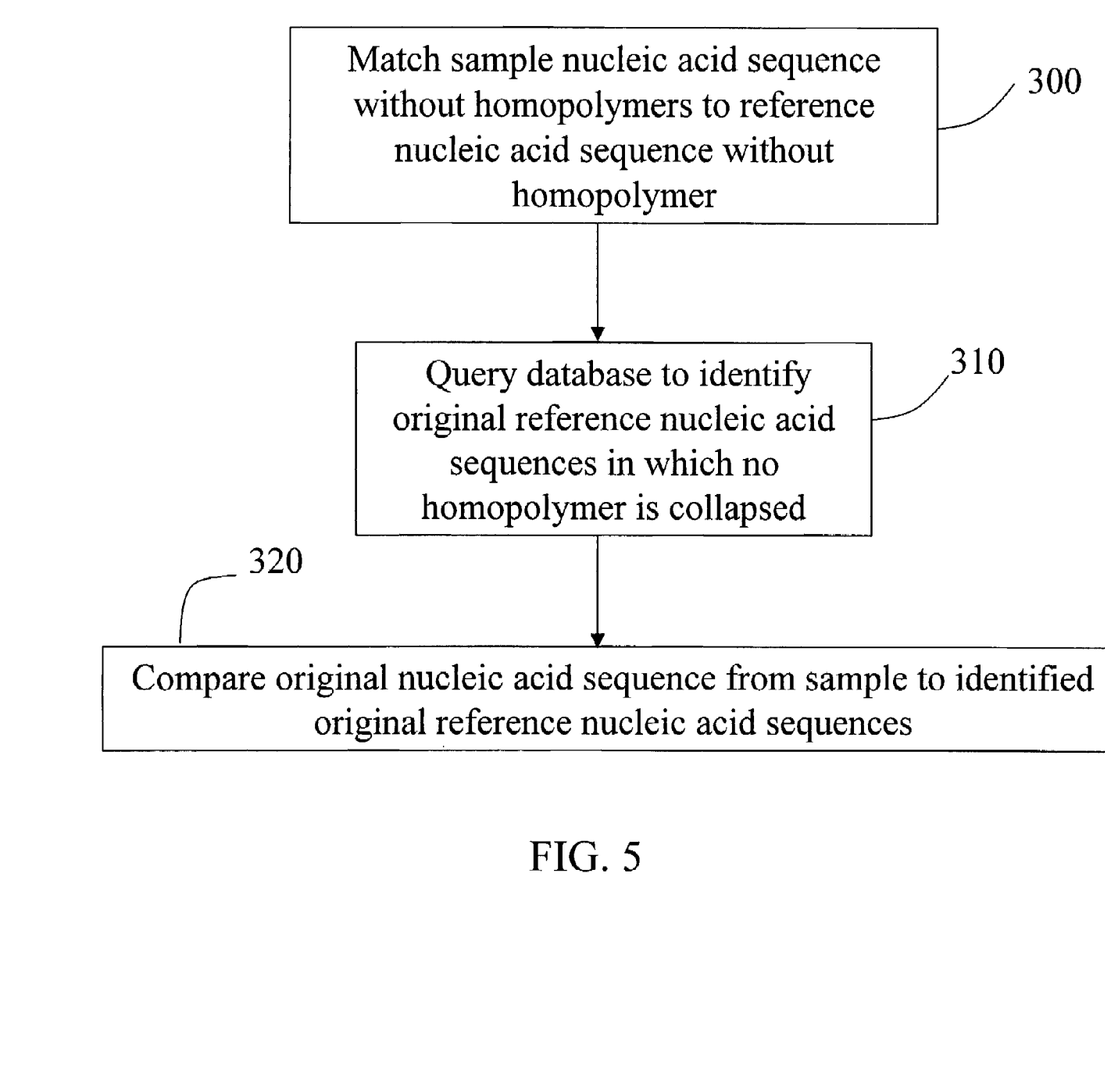
FIG. 5 is a flowchart depicting one exemplary nucleic acid matching process incorporating a subsequent comparison of original, non-collapsed sequences.

With reference to FIG. 5, an exemplary methodology that may be performed by one or more software processes executing on a digital data processing device 140 when comparing non-collapsed nucleic acid sequences is depicted. When a collapsed sample nucleic acid sequence matches an entry in a database of reference nucleic acid sequences without homopolymer regions (such as an entry in the table 146 of the database 144), (300) the information contained within the records of the database can be examined to identify if there are one or more original reference nucleic acid sequences in which no homopolymer was collapsed and that correspond to the entry. These original reference nucleic acid sequences (such as entries in the table 148) can then be compared to the original nucleic acid sequence from the sample (320), which original sample sequence itself could be stored by the digital data processing device 140.

Continuing with the example above, after a detected sample nucleic acid sequence "AAGGGCCT" is collapsed to sequence "AGCT" and the collapsed sample sequence is compared against and matched to a record in table 146 of database 144 by the digital data processing device 140, information can be read regarding the original reference nucleic acid sequence used when the database was created. In this case, the database record for "AGCT" includes a pointer to one or more positions in a separate table 148 of database 144. In this example, these positions in table 148 contain the three original reference nucleic acid sequences "AAAGGGCCT," "AAGGGCCT," and "AGCT." The originally detected sample nucleic acid sequence, "AAGGGCCT," is then compared to the three original reference nucleic acid sequences in table 148, and the second original reference nucleic acid sequence "AAGGGCCT" is identified as a match to the originally detected sample nucleic acid sequence.

Comparison element 320 in FIG. 5 identifies substantially identical original reference and original sample nucleic acids as matches. Because of the difficulties inherent in accurately measuring the length of a homopolymer using some sequencing methods, comparison element 320 can alternatively identify an original reference nucleic acid sequence that best matches an original sample nucleic acid sequence, even if the two are not substantially identical. A match can be selected, for example, by identifying a particular original reference nucleic acid sequence that best corresponds (e.g., exhibits a greater amount of matching nucleotides) to an original sample nucleic acid sequence that was obtained from a DNA sequencing reaction, Specifically, for each of the original reference nucleic acid sequences, the probability of sequencing errors yielding the observed original nucleic acid sequence from the sample can be calculated. The probability can be based, at least partly, on the sequencing method and conditions encountered and may be based on empirical observations and/or theoretical calculations. The original reference nucleic acid sequence of highest probability is selected as the matching sequence.

One exemplary way of determining the likelihood that one of a set of matching reference sequences is the correct sequence involves the use of Bayes theorem and probability concepts to arrive at an equation that yields a probability value for each candidate matching reference sequence. This equation is $P(S_i) = Omega_i/(\text{the sum over k of } Omega_k)$ where each k and the subscript i go from 1 to n, n being a positive integer. $S_i$ represents each of the n candidate matching reference sequences, and Omega represents the a priori probability of the sequencing machine generating the observed sequence using the measured sample and parameters.

EXAMPLE 1

Creation and Analysis of a Reference Nucleic Acid Sequence Database without Homopolymer Regions A set of mRNA nucleic acid sequences was identified as a starting point for creation of a reference nucleic acid sequence database. A computer program was run on the preexisting mRNA data. The program converted a copy of the mRNA data, substituting a single base letter for each homopolymer. The resulting data set was loaded into a database and the resulting database was tested against mRNA sequences in which homopolymer regions had been collapsed. The database properly recognized each of the collapsed mRNA sequences.

Figure 6:
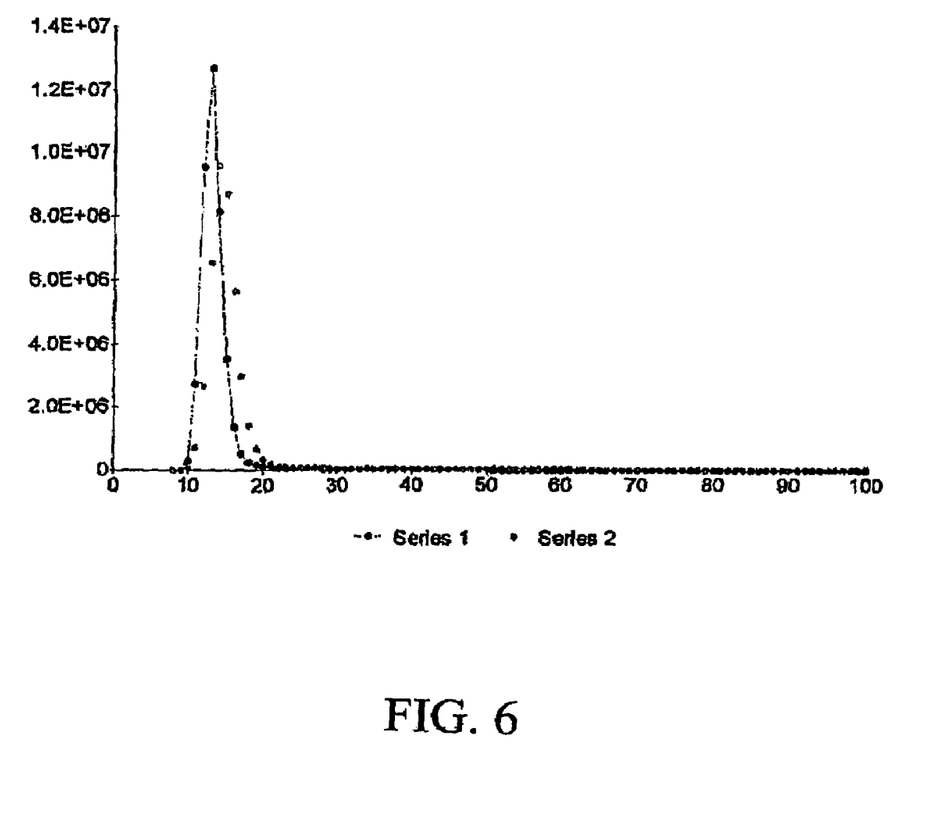
FIG. 6 is a histogram indicative of exemplary minimum lengths of unique sequences associated with an illustrative mRNA sequence, where "Series 1" corresponds to sequences in which no homopolymer regions have been collapsed and "Series 2" corresponds to sequences in which all homopolymer regions have been collapsed.

The database was then tested to ascertain the length of unique sequences stored in the database. A test program matched each mRNA and matched it at every position against the remainder of the database. The program found the sequence that matched the largest number of bases at that position and noted how many bases this was. The resulting data set is shown in FIG. 6 as a histogram of the number of sequences (on the Y axis) that are first unique at a given length. In the histogram, the unreduced, original data set is shown as "Series 1," in which the dots are connected by a line.

The reduced data set, without homopolymer regions, is shown as "Series 2," in which the dots are not connected by a line.

The sequences in the reduced data set require, on average, perhaps 2-3 extra bases in order to be rendered unique. This can be understood because the theoretical information content per base for the reduced data set should indeed be lower. Because, in most natural systems, a nucleic acid can have any of four values (A, C, G, or T/U), the first base encodes 2 bits of information. In the reduced data set without homopolymer regions, however, each subsequent base in the string can have only one of three values. (A subsequent base cannot have the same value as its preceding base; that would be observed only in a homopolymer.) Accordingly, each symbol after the first encodes only 1.5 bits in the reduced data set. On the other hand, normal DNA contains a higher number of repeats than would happen by random chance, limiting the actual difference in information content between the reduced and unreduced data sets.

EXAMPLE 2

Matching Sequenced Nucleic Acids to a Reduced Reference mRNA Sequence Database mRNA molecules isolated from a sample are converted to cDNA sequences by a reverse transcriptase reaction using known methods. The resulting cDNA molecules are sequenced by the Sanger method, by a sequencing-by-synthesis method, or other available DNA sequencing technology. For each molecule sequenced, each nucleotide detected is recorded in a string. A second string is then created to include the first string with all homopolymers collapsed (e.g. AACGT->ACGT). The resulting second strings are compared to the reduced/collapsed data set generated in Example 1 to identify the mRNA transcripts present in the isolate from the sample.

Variations, modifications, and other implementations of what is described herein will occur to those of ordinary skill in the art without departing from the spirit or scope of the invention. The invention is not limited to the preceding illustrative description.

What is claimed is:

1. A method of comparing nucleic acid sequences, wherein all of the following steps are performed on a computer, the method comprising:
   providing a nucleic acid sequence obtained from a sample and including at least one homopolymer region;
   collapsing each of the homopolymer regions to a single nucleotide to form a representative sample sequence without homopolymer regions; and
   comparing the representative sample sequence to at least one of a plurality of collapsed reference nucleic acid sequences without homopolymer regions to determine whether the representative sample sequence matches one of the plurality of reference nucleic acid sequences; and
   providing results of the comparing step to a user.

2. The method of claim 1, wherein the steps of collapsing and comparing include the use of indexes and a binary search to determine whether the representative sample sequence matches one of the plurality of reference nucleic acid sequences.

3. The method of claim 1, wherein each of the plurality of reference nucleic acid sequences comprises a cDNA or RNA sequence.

4. A method of matching nucleic acid sequences, wherein all of the following steps are performed on a computer, the method comprising:

collapsing each homopolymer region of a patient nucleic acid sequence to a single nucleotide to form a representative sample sequence; and     determining whether the representative sample sequence matches a member of a database of reference nucleic acid sequences without homopolymer regions, at least one of the reference nucleic acid sequences created by collapsing at least one homopolymer region to a single nucleotide, at least some of the reference nucleic acid sequences being indicative of a diagnosis or prognosis;

providing results of the determining step to a user.

5. The method of claim 4, wherein the steps of collapsing and determining include the use of indexes and a binary search to determine whether the representative sample sequence matches a member of the database of reference nucleic acid sequences.

\* \* \* \* \*